United States Patent [19]

Yoshizawa et al.

[11] Patent Number: 5,175,322
[45] Date of Patent: Dec. 29, 1992

[54] CONTINUOUS PROCESS FOR PREPARING METALLIC SOAPS

[75] Inventors: Fumihiko Yoshizawa, Hyogo; Fumio Kikuchi, Kanagawa; Seiichi Kojima; Kenichi Yuasa, both of Hyogo, all of Japan

[73] Assignee: Nippon Oil and Fats Co., Ltd., Tokyo, Japan

[21] Appl. No.: 441,593

[22] Filed: Nov. 27, 1989

[51] Int. Cl.$^5$ .............................................. C07F 3/00
[52] U.S. Cl. ....................... 554/71; 554/72; 554/73; 554/74; 554/75; 554/76; 562/606; 252/367; 252/368
[58] Field of Search ............... 260/414; 562/609, 606; 554/71, 72, 73, 74, 75, 76; 252/367, 368

[56] References Cited

U.S. PATENT DOCUMENTS 2,417,071  3/1947  Gebhart et al. ............... 260/414
4,235,794  11/1980  Rieber et al. ................. 260/414
4,307,027  12/1981  Barzelli et al. ............... 252/369

FOREIGN PATENT DOCUMENTS 1126033  9/1968  United Kingdom .

OTHER PUBLICATIONS

Chemical Abstracts, vol. 85, #4, 1976, p. 92.

*Primary Examiner*—Jose G. Dees
*Assistant Examiner*—Deborah Carr
*Attorney, Agent, or Firm*—Sughrue, Mion, Zinn, Macpeak & Seas

[57] ABSTRACT

A continuous process for preparing a metallic soap by a double decomposition process is disclosed, in which an aqueous solution of an alkali soap and an inorganic metal salt are separately fed directly on the surface of the rotating impeller of a mixer to instantaneously mix them together and the resulting metallic soap aqueous slurry is discharged out from the mixer without delay. Metallic soaps free from contamination with unreacted starting materials or by-products can be continuously obtained using small-sized reactor vessels with a reduced energy.

5 Claims, 1 Drawing Sheet

CONTINUOUS PROCESS FOR PREPARING METALLIC SOAPS

FIELD OF THE INVENTION

This invention relates to a continuous process for preparing metallic soaps of high quality according to a double decomposition process or precipitation process.

BACKGROUND OF THE INVENTION

Known techniques for the production of metallic soaps are roughly divided into a fusion process and a double decomposition process. The fusion process comprises directly reacting a fused fatty acid and a metal oxide or a metal hydroxide to obtain a metallic soap. The double decomposition process comprises reacting an aqueous solution of an alkali soap comprising an alkali metal salt or ammonium salt of a fatty acid (hereinafter simply referred to as "alkali soap") with an inorganic metal salt.

Although the fusion process has merits relating to reactor vessels in that the steps involved are simple so that small-sized reactor vessels suffice for carrying out the process, it has a number of disadvantages: (a) The reaction hardly reaches completion so that the resulting metallic soap contains unreacted fatty acid and metal oxide or hydroxide in considerable quantities. (b) Since the reaction proceeds in high temperatures, the resulting metallic soap is slightly colored. (c) The metallic soap obtained is contaminated with different metals derived from the starting metal oxide or metal hydroxide, e.g., iron, lead, cadmium, and manganese, to a not inconsiderable extent. (d) The product obtained generally has a large particle size, and high labor is required for grinding the coarse particles to obtain a desired particle size.

To the contrary, the double decomposition process has merits relating to product quality, i.e., reduced contents of unreacted materials and different metals, a satisfactory hue, and fineness of the product. It involves, however, disadvantages: (a) Large-sized reactor vessels are required. (b) The reaction slurry shows unstable dispersibility in water, thus deteriorating workability. (c) Water-soluble salts remain in the resulting metallic soap.

Hence, various processes for overcoming the above-described disadvantages associated with the fusion process or double decomposition process have been studied. For example, it has been recommended to carry out the fusion process in the presence of a surface active agent as disclosed in JP-B-60-21573 (the term "JP-B" as used herein means an "examined published Japanese patent application") or under reduced pressure as disclosed in JP-B-61-39296. Even by these proposals, however, the unreacted fatty acid and metal oxide or metal hydroxide as raw materials still remain in the product, though not so serious as in the conventional direct process, failing to obtain product quality on the same level as attained in the double decomposition process. Similarly, it has been suggested to carry out the double decomposition process in the presence of a surface active agent as disclosed in JP-B-51-44002. However, the product cannot be obtained without contamination of the surface active agent used. While the slurry concentration can be increased twice as much as that of the conventional double decomposition process, since the process is carried out in a batch-wise operation, large-sized reactor vessels are still required.

Several processes for continuously preparing metallic soaps have hitherto been reported. For example, British Patent 693,741 describes a continuous process for producing an aluminum soap by double decomposition. This process is carried out using four vessels arranged in series with overflow connections. To a first vessel are continuously fed an aqueous sodium soap solution and an aqueous solution of aluminum sulfate at $[Al_2(SO_4)_3]$ substantially equivalent feed rates (assuming that 2 mols of a carboxyl group react per mol of an aluminum atom) to conduct a double decomposition reaction. The reaction product is then forwarded to a second vessel, where an excess of an aqueous solution of $Al_2(SO_4)_3$ is added [11 to 13% excess, calculated as aluminum oxide $(Al_2O_3)$]. The reaction product is further forwarded to a third vessel and then to a fourth vessel continuously and aged thereby to increase the particle size of an aluminum soap in a easily filterable form.

According to this process, the reaction in the first vessel should be carried out with vigorous agitation with no reference to the structure of the reaction vessel to be used. That is, the production process is designed so that the reaction slurry continuously passes through batchwise reaction vessels connected in series. Therefore, the process enjoys no merit of size reduction of plant which should have been resulted from a continuous process. Further, it is described that the particle size is increased while mixing at an elevated temperature. However, from the fact that the mixing is carried out with the starting metal salt, $Al_2(SO_4)_3$, being present in a large excess, this process cannot be regarded practical taking into consideration removal of the excess of the starting material in the working-up stage, an increase of the metal content in the final product, and a consumption of the starting material.

JP-A-56-169642 (the term "JP-A" as used herein means an "unexamined published Japanese patent application") describes a process for continuously preparing metallic soaps by a wet fusion process, comprising mixing an aqueous emulsion of a fatty acid and an aqueous dispersion of a basic metal carbonate under a high shearing condition to continuously obtain an aqueous slurry of a metallic soap. An aqueous slurry of a metallic soap is a so-called Bingham fluid which has a low viscosity with fluidity with only the external force applied, but increases its viscosity and loses fluidity when released from the external force.

The apparatus employed in the above-described wet fusion process has such a structure that the two liquids as raw materials may meet in a pipe and then be forwarded to a part where a high shear force is imposed. In other words, the two liquids are not fed directly to the part under a high shear force. It is considered therefore that a metallic soap is generated in the place where the liquids meet and the slurry containing the thus generated metallic soap increases in viscosity to lose fluidity, which would clog the pipe, ultimately resulting in a failure of continuously using the apparatus. Besides, since the apparatus uses a mixer having no self-discharge ability without any consideration given to discharge of the aqueous slurry after mixing under a high shearing condition, there is a fear that the mixer is accumulated with the thickened slurry and finally fails to be used. From all these considerations, when such an apparatus is applied to a double decomposition process, it is impossible to perform continuous production due to clogging.

Further, this process has a problem of incompleteness of the reaction from the very nature of a fusion process. It is thus considered that the product contains a large quantity of a free fatty acid or the starting basic metal carbonate, but the disclosure has no reference to this point. Furthermore, the process requires pre-treatments of the starting materials to prepare an aqueous emulsion of the fatty acid and an aqueous dispersion of the basic metal carbonate, and ammonia is used for the pre-treatments. A washing step is therefore required in practice to remove ammonia or an ammonium salt of the fatty acid, thus increasing the steps in number. Moreover, it is difficult to completely remove ammonia from the product. The odor of ammonia remaining in the product also give rise to a problem.

U.S. Pat. No. 4,307,027 describes a continuous fusion process comprising continuously feeding a fatty acid and a metal oxide or a metal hydroxide to a stirred-tank reactor, mixing them in a molten condition to conduct a reaction, continuously feeding the reaction mixture to a plug flow reactor to continue the reaction to continuously discharge a solid or pasty metallic soap from a discharge orifice. According to the process, though a metallic soap can be prepared in compact reactor vessels, the product is contaminated with large amounts of impurities in the very nature of a fusion process. More specifically, the product contains residual metal oxide or metal hydroxide starting material in an amount higher than the theoretical one by 1 to 1.5% by weight on an ash basis conversion.

Hence, while a number of proposals have been made on the continuous production of metallic soaps as stated above, a commercially practicable continuous process by which a metallic soap having high quality on the same level with the product obtained by a double decomposition process can be obtained using reactor vessels of reduced size has not yet been developed.

As described above, processes for preparing metallic soaps include a fusion process and a double decomposition process which have both merits and demerits, but the latter process has high merits of product quality and is recognized as superior as compared with the former process.

If the disadvantages of the double decomposition process can be overcome, there would be established an industrially favorable process for the production of metallic soaps. The disadvantages inherent to the double decomposition process are described in more detail as hereunder.

(a) The slurry concentration during the preparation process is as low as 5 to 13% by weight, and the process is batchwise. As a result, the volume of the reactor vessel is required about 10 times of the production volume, and also a vast amount of energy is needed.

(b) The aqueous slurry of a metallic soap after a double decomposition reaction is instable. Should a feed rate of the inorganic metal salt exceed a given value (varying depending on the kind of the metallic soap) during the reaction, the produced metallic soap shows water repellency and floats completely apart from an aqueous layer, making workability extremely poor.

(c) The metallic soap after the double decomposition reaction is contaminated with unreacted alkali soap and inorganic metal salt and a by-produced alkali metal salt or ammonium salt. These impurities cannot be removed completely even through the subsequent washing step.

As a result, a water-soluble matter remains in the product, and causes water absorption of the product and turbidity on fusion of the product.

SUMMARY OF THE INVENTION

Accordingly, an object of this invention is to overcome the above-described disadvantages of the conventional double decomposition process and to provide a process by which a high quality metallic soap can be prepared in a continuous method with simple and small-sized reactor vessels.

As a result of extensive studies, the present inventors have found that the above object of this invention is accomplished by adding special devices to a mixer in which a double decomposition reaction is carried out, more specifically a means for feeding an alkali soap aqueous solution and an inorganic metal salt and a means for discharging the reaction product out of the mixer.

The present invention relates to a continuous process for preparing a metallic soap by a double decomposition process, in which an aqueous solution of an alkali soap and an inorganic metal salt are separately fed directly on the surface of rotating impeller of a mixer to instantaneously mix them together and the resulting reaction mixture is discharged from the mixer without delay.

DETAILED DESCRIPTION OF THE INVENTION

Figure 1:
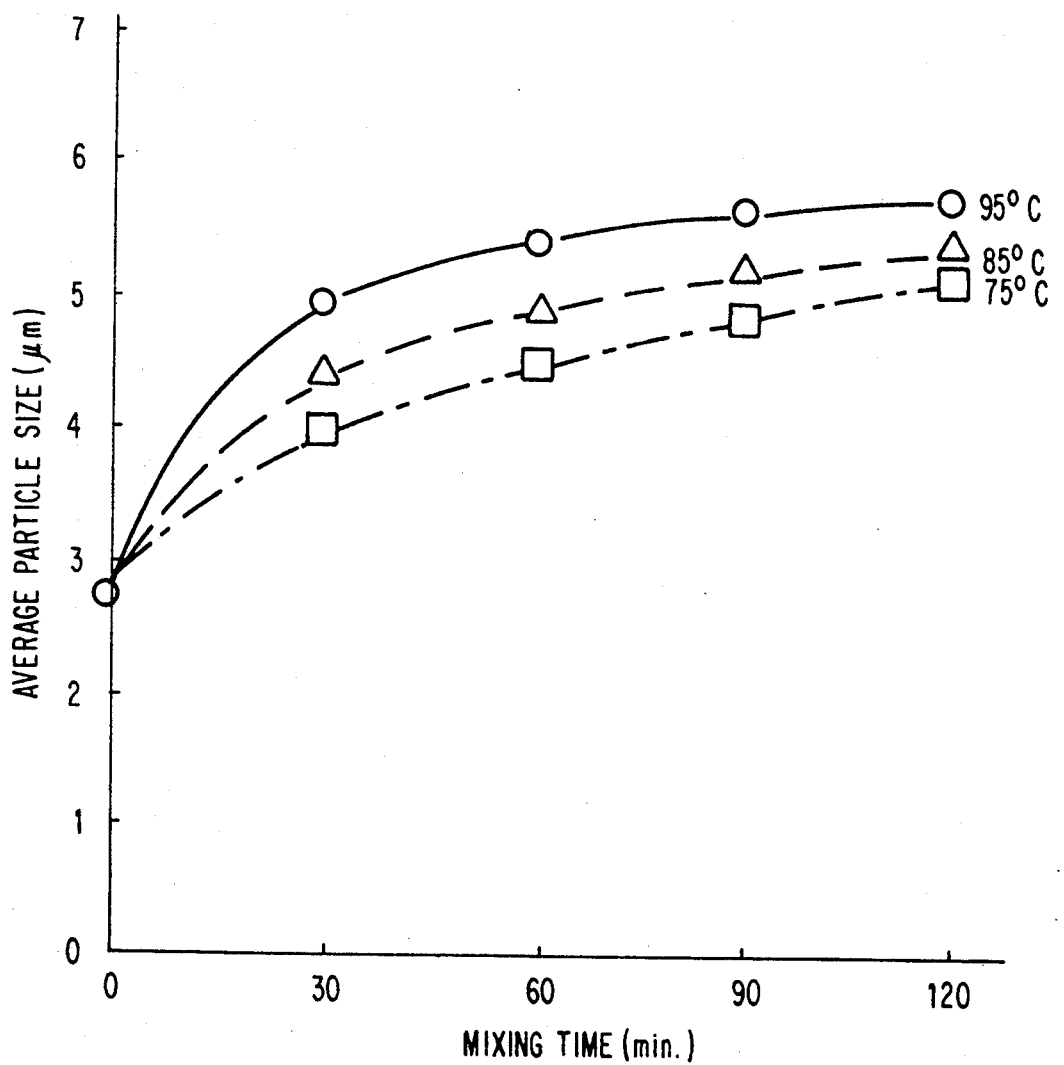
FIG. 1 illustrates a characteristic diagram of average particle size of calcium stearate obtained in Example 5 of the present invention vs. mixing conditions (time and temperature).

The alkali soap which can be used in the present invention includes an alkali metal salt of a fatty acid and an ammonium salt of a fatty acid. Examples of alkali soaps are alkali metal or ammonium salts of fatty acids having from 6 to 22 carbon atoms, e.g., caproic acid, caprylic acid, capric acid, lauric acid, myristic acid, palmitic acid, stearic acid, arachidic acid, behenic acid, isostearic acid, oleic acid, linoleic acid, linolenic acid, ricinoleic acid, and 12- hydroxystearic acid, or mixtures thereof. Processes for preparing such alkali soaps are not particularly limited and may be either in a batch system or in a continuous system. Taking the merit on reactor vessels as a whole into consideration, a continuous system is preferred.

Inorganic metal salts which can be used in the present invention include water-soluble metal salts, e.g., a hydrochloride, a sulfate, a nitrate or an acetate of magnesium, calcium, strontium, barium, zinc, cadmium, lead, aluminum, copper, iron or cobalt, or mixtures thereof.

The process according to the present invention is characterized in that an alkali soap aqueous solution and an inorganic metal salt in the form of a powder or an aqueous solution are separately fed directly on the surface of the rotating impeller of a mixer in a continuous manner by means of a constant delivery feeder or pump and instantaneously dispersed and mixed together, and the produced metallic soap aqueous slurry is immediately and continuously discharged from the mixer with, for example, a scraper blade fixed on the rotor without being accumulated in the mixer.

In general, a double decomposition reaction has a high reaction rate, and in the moment the above-described two starting materials meet a metallic soap is produced. Further, the aqueous slurry of the metallic soap resulted from the double decomposition reaction is, as mentioned above, a so-called Bingham fluid which has a low viscosity and exhibits fluidity under an external force but increases its viscosity and loses fluidity without the external force. Therefore, if the two starting materials are not separately fed on the surface of rotating impeller of a mixer, i.e., if they meet together in a place where no mixing force is applied, e.g., a pipe, before they reach the rotor, a metallic soap is generated at a moment, increases the viscosity of the slurry to lose fluidity, and accumulates that part. If the thus accumulated metallic soap aqueous slurry is not discharged from the mixer immediately after the reaction, i.e., if in using a mixer having no self-discharge ability and incapable of rapidly discharging the slurry, such as a static mixer, a line mixer, and a line mill, the mixer is clogged with the aqueous slurry.

To the contrary, since in the present invention the two starting materials are separately fed on the surface of rotating impeller of a mixer, and the reaction product is immediately discharged from the mixer without clogging the mixer, the above-described troubles, i.e., clogging of pipings before the starting materials are fed to the mixer and accumulating of the product slurry in the mixer, do not occur at all, thereby making it feasible to continuously carry out the metallic soap production.

The number of impellers in the mixer which can be used in the present invention is selected so that the two starting materials are sufficiently dispersed and mixed while acquiring a sufficient discharge ability. As a mixer a pump with turbine blades may be used in this invention. In using a pump of this type, it is important that the two starting materials should be separately supplied directly on the surface of rotating turbine blades in the suction side and the pipe in the delivery side should be wide and short as possible so as to reduce resistance.

The concentration and temperature of the alkali soap aqueous solution to be fed are so selected as to sufficiently maintain water-solubility of the alkali soap, while varying depending on the kind of the alkali soap. For example, an aqueous solution of sodium stearate, a commonly employed alkali soap, suitably has a concentration of from 5 to 20% by weight and a temperature of from 70° to 100° C. Too a low concentration disadvantageously reduces the concentration of the resulting metallic soap aqueous slurry.

The inorganic metal salt may be fed either in the form of a powder or in the form of an aqueous solution or aqueous slurry thereof. When fed as an aqueous solution, the concentration and temperature are selected so that the inorganic metal salt should keep the dissolved state in water. More specifically, the concentration of the aqueous solution ranges from 5 to 80% by weight, preferably from 10 to 50% by weight. If it is less than 5% by weight, the resulting metallic soap aqueous slurry has a reduced concentration. An aqueous solution having a concentration exceeding 80% by weight is difficult to feed.

An equivalent ratio of the inorganic metal salt and alkali soap usually ranges from 0.95 to 1.05. At equivalent ratios out of this range, the amounts of unreacted starting materials would be increased, readily contaminating the product. More strictly, the inorganic metal salt/alkali soap equivalent ratio varies depending on the kind of the metallic soap produced. For example, in the production of calcium stearate, it is in the range of from 1.00 to 1.05, preferably from 1.00 to 1.02. If it is less than 1.00, the amount of residual alkali soap which is hardly removed in the subsequent washing step increases. On the other hand, if it exceeds 1.05, the slurry becomes instable with the metallic soap floating on the aqueous layer. In the production of zinc stearate, the inorganic metal salt/alkali soap equivalent ratio ranges from 0.95 to 1.00, preferably from 0.98 to 1.00. If it is out of this range, the same disadvantages as described above take place.

Suitable concentrations of the metallic soap aqueous slurry produced by the process of this invention may much depend on the kind of the metallic soap.. In the case of calcium stearate or zinc stearate, the concentration usually ranges from 5 to 20% by weight, preferably from 8 to 15% by weight. Too a low concentration is accompanied with a disadvantage relating to reactor scale in spite of a continuity of the process, and too a high concentration, i.e., too a high viscosity, of the slurry deteriorates handling properties.

The thus produced metallic soap aqueous slurry is then subjected to filtration, washing, and drying in a usual manner. If desired, the product is further subjected to milling. The resulting metallic soap particles have a characteristically small average particle size usually ranging from 2.5 to 3.5 $\mu$m, smaller than that of conventional particles having a size of from 4.5 to 5.5 $\mu$m.

The inventors have continued their studies to obtain metallic soap particles having an increased particle size over the above-recited range. As a result, it has been discovered that the particles are increased in size with time by continuing mixing of the aqueous slurry under heating. For example, mixing of the slurry at a temperature of 95° C. for a period of 30 minutes results in the production of particles having a size equal to the conventional products. By changing the mixing time or temperature, metallic soap particles of various sizes can be obtained.

Metallic soaps used in powder metallurgy or pigment dispersing are required to have various particle sizes according to use. Conventional double decomposition processes permitted of no delicate control of particle size, whereas the process of the present invention in which mixing is continued under heating enables us to easily obtain a metallic soap having a desired particle size meeting demand.

Mixing of the slurry can be carried out in a continuous manner by employing a reactor vessel equipped with a plurality of impellers and an overflow discharge outlet. The metallic soap aqueous slurry obtained under the aforesaid conditions is subjected to mixing as such, requiring no addition of an excess of inorganic metal salt or alkali soap. Mixing is usually performed at a temperature of from 50° to 100° C., preferably from 70° to 90° C. The effect of increasing the particle size cannot be produced by mixing at lower temperatures. The higher the mixing temperature, the shorter the time required for reaching a desired particle size.

From the very nature of the metallic soap aqueous solution as a Bingham fluid as stated above, the present invention is designed in such a manner that an alkali soap aqueous solution and an inorganic metal salt are separately fed directly on the surface of rotating impeller of a mixer and that the produced aqueous slurry of metallic soap is rapidly discharged from the mixer, thereby continuously preparing a metallic soap aqueous slurry in a stable manner without causing clogging of the starting material feed passages and the inside of the mixer.

In addition, because the alkali soap aqueous solution and inorganic metal salt are dispersed by the impellers of the mixer and momentarily mixed together, incorporation of free alkali soap, free inorganic metal salt, or by-produced alkali metal salt or ammonium salt into the final product can be substantially prevented.

While the particle size of the metallic soap obtained by the process of this invention is smaller than those obtained by conventional batch systems, it is increased with time by mixing under heating. Even if the mixing time is prolonged beyond a certain period, no further effect is produced so that the particle size does not exceed a certain limit. The mechanism of these phenomena has not yet been made clear.

The effects brought about by the process of the invention are summarized as follows:

(a) An aqueous slurry of a metallic soap can be prepared continuously through a double decomposition process. Thus, huge reactor vessels as used in the conventional batchwise double decomposition processes are not required. Namely, simple reactor vessels composed of a mixer and a small-sized aging tank would suffice for carrying out the production, greatly reducing the plant cost of reactor vessels. Continuity of the process also cuts the cost of energy.

(b) The metallic soap particles in the aqueous slurry obtained by the present invention are not substantially contaminated with a free alkali soap. The free alkali soap serving as a surface active agent is present in the slurry in a uniformly dissolved state. Therefore, when compared with the conventional double decomposition processes in which the excess of an alkali soap should be controlled based on experience while observing the dispersion state of the reaction slurry, in the present invention a stable metallic soap aqueous slurry which hardly undergoes floating can always be obtained in the presence of a small amount of a free alkali soap, thus achieving markedly improved workability.

(c) The metallic soap aqueous slurry prepared by the process of the invention is subjected to filtration, washing, drying and, if desired, milling in a usual manner to obtain the final product. Since the metallic soap particles are not substantially contaminated with a free alkali soap, a free inorganic metal salt, or a by-produced alkali metal salt or ammonium salt, these impurities can easily be removed by washing with a small quantity of water to obtain a metallic soap having a reduced water-soluble content. This effect is particularly pronounced in the preparation of zinc stearate.

(d) The metallic soap particles in the aqueous slurry as obtained by the process of the invention may have the size thereof increased by mixing under heating so as to obtain particles having a particle size not only equal to those obtained by conventional batchwise double decomposition processes but also variable according to the final use. In particular, it is possible to obtain particles having a smaller size than those obtained by the conventional batchwise double decomposition processes.

The process of the present invention thus overcome the disadvantages of the conventional double decomposition processes and provides a metallic soap having high quality and various particle sizes.

The present invention is now illustrated in greater detail by way of the following Examples, but it should be understood that the present invention is not deemed to be limited thereto. All percentages are given on a weight basis unless otherwise specified.

EXAMPLE 1

In a 500 l-volume reaction vessel were charged 50 kg of stearic acid (neutralization value: 200), 14.9 kg of 48% sodium hydroxide, and 385 kg of water and mixed at 90° C. for 30 minutes to prepare a 12% aqueous solution of sodium stearate (hereinafter referred to as Na-St).

The Na-St aqueous solution and a 20% calcium chloride aqueous solution were continuously, separately and vertically fed on the surface of rotating impeller from a suction of centrifugal pump "CSX-503" (manufactured by Kabushikikaisha Torishima Seisakusho; discharge: 0.25 m$^3$/min × 10 mH; number of revolutions: 3600 rpm) for 4.5 hours at a rate of 100 kg/hr and 12.1 kg/hr, respectively, using respective constant delivery pumps to prepare an aqueous slurry of calcium stearate (hereinafter referred to as Ca-St). The CaCl$_2$/Na-St equivalent ratio was 1.02.

The centrifugal pump used above had turbine impellers and was set vertically. The piping on the supply side (suction side) was so designed that the two starting solutions might be separately fed directly onto the surface of the rotating turbine impellers, and the piping on the discharge side was designed to be as wide and short as possible so that the reaction slurry could not accumulate in the pump.

The resulting Ca-St aqueous slurry was continuously mixed in a mixing tank equipped with two impellers at 90° C. for a residence time of 1 hour. The aqueous slurry was then filtered in a filter press and washed with water in an amount 5 times the volume of the Ca-St dry powder. The resulting wet cake had a water content of 33%. The wet cake was dried in a hot-air drier set at 105° C. to obtain a Ca-St powder. The Ca-St powder had a water-soluble content of 0.18% and an average particle size of 5.3 μm.

EXAMPLE 2

A 12% Na-St aqueous solution as prepared in the same manner as in Example 1 and a 20% zinc sulfate aqueous solution were continuously fed to the same centrifugal pump as used in Example 1 at feed rates of 100 kg/hr and 15.8 kg/hr, respectively, for 4.5 hours using respective constant delivery pumps to obtain an aqueous slurry of zinc stearate (hereinafter referred to as Zn-St). The ZnSO$_4$/Na-St equivalent ratio was 0.99.

The Zn-St slurry was then continuously mixed in the same manner as in Example 1, filtered in a filter press, and washed with warm water at 60° C. in an amount 10 times the volume of the Zn-St dry powder. The resulting wet cake had a water content of 26%. The wet cake was dried in a hot-air drier at 105° C. to obtain a Zn-St powder. The Zn-St powder had a water-soluble content of 0.39% and an average particle size of 5.7 μm.

EXAMPLE 3

In a 500 l-volume reaction vessel were charged 55 kg of stearic acid (neutralization value: 200), 16.3 kg of 48% sodium hydroxide, and 352 kg of water and mixed at 90° C. for 30 minutes to prepare a 14% aqueous solution of Na-St. The Na-St aqueous solution and a 35% calcium chloride aqueous solution were continuously fed to the same centrifugal pump as used in Example 1 at feed rates of 1600 kg/hr and 120 kg/hr, respectively, for 15 minutes using respective constant delivery pumps to obtain a Ca-St aqueous slurry. The CaCl$_2$/Na-St equivalent ratio was 1.02.

Part of the resulting Ca-St aqueous slurry was withdrawn and further mixed at 90° C. for 1 hour, filtered in a filter press, and washed with water in an amount 5 times the volume of the Ca-St dry powder to obtain a wet cake having a water content of 34%. The wet cake was dried in a hot-air drier at 105° C. to obtain a Ca-St powder. The Ca-St powder had a water-soluble content of 0.22% and an average particle size of 5.0 μm.

EXAMPLE 4

Stearic acid (neutralization value: 200), 20% sodium hydroxide, and warm water at 90° C were continuously fed to a line homomixer at feed rates of 10.0 kg/hr, 7.13 kg/hr, and 72.9 kg/hr, respectively, using respective constant delivery pumps to prepare a 12% Na-St aqueous solution, which was continuously forwarded from the outlet to the same centrifugal pump as used in Example 1 where it was mixed with a 20% calcium chloride aqueous solution fed at a rate of 10.1 kg/hr using a constant delivery pump to obtain a Ca-St aqueous slurry. The $CaCl_2$/Na-St equivalent ratio was 1.02.

The resulting Ca-St aqueous slurry was mixed, filtered, washed, and dried in the same manner as in Example 1 to obtain a Ca-St powder having a water-soluble content of 0.23% and an average particle size of 4.9 μm.

COMPARATIVE EXAMPLE 1

A 12% Na-St aqueous solution prepared in the same manner as in Example 1 and a 20% calcium chloride aqueous solution were fed to a centrifugal pump at feed rates of 100 kg/hr and 12.1 kg/hr, respectively, using respective constant delivery pumps. The centrifugal pump used here was different from that of Example 1 in that the piping on the supply side was so designed that the two solutions might meet during the passage through the piping and then supplied to the turbine blades. For 1 minute from the beginning of feeding, there was discharged a Ca-St aqueous slurry. Thereafter, the Ca-St clogged the piping on the supply side, making it impossible to further continue the reaction.

COMPARATIVE EXAMPLE 2

A 12% Na-St aqueous solution prepared in the same manner as in Example 1 and a 20% calcium chloride aqueous solution were fed to a line mill at feed rates of 80 kg/hr and 9.6 kg/hr, respectively, using respective constant delivery pumps. The line mill used had no strong self-discharge ability. For 10 minutes from the starting of feeding, a Ca-St aqueous slurry was discharged, but thereafter, the mill was accumulated with Ca-St, making it impossible to further continue the reaction. On observation of the inside of the mill, the hollow part in the rear of the part where a shear force was imposed was found to be densely accumulated with Ca-St.

COMPARATIVE EXAMPLE 3

In a 500 l-volume reaction vessel were charged 45 kg of stearic acid (neutralization value: 200), 13.4 kg of 48% sodium hydroxide, and 347 kg of water and mixed at 90° C. for 30 minutes to prepare a 12% Na-St aqueous solution. To the aqueous solution (90° C.) was added 45.4 kg of a 20% calcium chloride aqueous solution over a period of 30 minutes, followed by mixing at 90° C. for 30 minutes to obtain a Ca-St aqueous slurry. The $CaCl_2$/Na-St equivalent ratio was 1.02.

The resulting aqueous slurry was filtered in a filter press and washed with water in an amount twice the volume of the Ca-St dry powder to obtain a wet cake having a water content of 31%. The wet cake was dried in a hot-air drier at 105° C. to obtain a Ca-St powder having a water-soluble content of 0.31% and an average particle size of 5.1 μm.

COMPARATIVE EXAMPLE 4

The same procedure of Comparative Example 3 was repeated, except that the 12% Na-St aqueous solution was kept at 70° C. and the slurry was subjected to dehydration (followed by washing and drying) immediately after the addition of calcium chloride aqueous solution. The resulting Ca-St powder had an average particle size of 4.4 μm. In a batchwise reaction it was difficult to control the particle size below this value.

COMPARATIVE EXAMPLE 5

A 12% Na-St aqueous solution kept at 90° C. as prepared in the same manner as in Comparative Example 3 was put in a 500 l-volume reaction vessel, and 62.8 kg of a 20% zinc sulfate aqueous solution was added thereto over 30 minutes, and the mixture was mixed at 90° C. for 30 minutes to obtain a Zn-St aqueous slurry. The $ZnSO_4$/Na-St equivalent ratio was 0.97.

The aqueous slurry was filtered in a filter press and washed with warm water at 60° C. in an amount ten times the volume of the Zn-St dry powder to obtain a wet cake having a water content of 28%. The wet cake was dried in a hot-air drier at 105° C. to obtain a Zn-St powder having a water-soluble content of 0.92% and an average particle size of 6.0 μm.

COMPARATIVE EXAMPLE 6

A 12% Na-St aqueous solution at 90° C. as prepared in the same manner as in Comparative Example 3 was placed in a 500 l-volume reaction vessel, and 63.4 kg of a 20% zinc sulfate aqueous solution was added thereto over 30 minutes. In several minutes from the completion of addition, the Zn-St layer floated completely apart from the aqueous layer, and could not be subjected to the successive treatments. The $ZnSO_4$/Na-St equivalent ratio was 0.98.

The results of Examples 1 to 4 and Comparative Examples 1 to 6 are shown in Table 1 below. The results of Table 1 clearly demonstrate the superiority of the process according to the present invention. In Table 1, "LM" is a line mill, and "P-1" and "P-2" are centrifugal pumps. The P-1 has such a design that two starting materials are separately fed to the turbine blades and piping in the discharge side has a reduced resistance. The P-2 has such a design that two starting materials are mixed in the pipe and then supplied to the turbine blades and the piping in the discharge side has a reduced resistance similarly to the P-1.

TABLE 1

| Example No. | Metallic Soap | Reaction Manner | Mixer used | Equiv. Ratio | Water-Soluble Content (%) | Average Particle Size (μm) |
| --- | --- | --- | --- | --- | --- | --- |
| Example 1 | Ca-St | continuous | P-1 | 1.02 | 0.18 | 5.3 |

TABLE 1-continued

| Example No. | Metallic Soap | Reaction Manner | Mixer used | Equiv. Ratio | Water-Soluble Content (%) | Average Particle Size (μm) |
| --- | --- | --- | --- | --- | --- | --- |
| Example 2 | Zn-St | continuous | P-1 | 0.99 | 0.39 | 5.7 |
| Example 3 | Ca-St | continuous | P-1 | 1.02 | 0.22 | 5.0 |
| Example 4 | Ca-St | continuous | P-1 | 1.02 | 0.23 | 4.9 |
| Comparative Example 1 | Ca-St | continuous | P-2 | 1.02 | production was impossible due to clogging of the supply side | |
| Comparative Example 2 | Ca-St | continuous | LM | 1.02 | production was impossible due to clogging of the mixer | |
| Comparative Example 3 | Ca-St | batchwise | — | 1.02 | 0.31 | 5.1 |
| Comparative Example 4 | Ca-St | batchwise | — | 1.02 | — | 4.4 |
| Comparative Example 5 | Zn-St | batchwise | — | 0.97 | 0.92 | 6.0 |
| Comparative Example 6 | Zn-St | batchwise | — | 0.98 | Zn-St separated and floated immediately after the reaction | |

EXAMPLE 5

One kilogram of the Ca-St aqueous slurry prepared in the centrifugal pump in Example 1 was withdrawn from the outlet and mixed in a 2 l flask under conditions shown in Table 2 below. The slurry was filtered using a Buchner funnel under reduced pressure, washed while being on the filter with 500 ml of water, and then dried in a hot-air drier. The average particle size of the resulting Ca-St powder is shown in Table 2 below.

TABLE 2

| Run No. | Mixing Temperature (°C.) | Mixing Time (min) | Average Particle Size (μm) |
| --- | --- | --- | --- |
| 1 | 75 | 30 | 4.0 |
| 2 | 75 | 60 | 4.6 |
| 3 | 75 | 90 | 4.9 |
| 4 | 75 | 120 | 5.3 |
| 5 | 85 | 30 | 4.5 |
| 6 | 85 | 60 | 5.0 |
| 7 | 85 | 90 | 5.3 |
| 8 | 85 | 120 | 5.5 |
| 9 | 95 | 30 | 5.0 |
| 10 | 95 | 60 | 5.5 |
| 11 | 95 | 90 | 5.8 |
| 12 | 95 | 120 | 5.9 |
| 13 | No mixing was conducted | | 2.7 |

The relationship between the mixing time and the average particle size of the resulting metallic soap particles is shown in FIG. 1 with temperature as a parameter. In FIG. 1, the marks of cubes, triangles and circles indicate curves of 75° C., 85° C., and 95° C., respectively. It can be seen from the results of Table 2 and FIG. 1 that Ca-St particles of various particle sizes can be obtained by varying the temperature and time of mixing.

While the invention has been described in detail and with reference to specific embodiments thereof, it will be apparent to one skilled in the art that various changes and modifications can be made therein without departing from the spirit and scope thereof.

What is claimed is:

1. A continuous process for preparing a metallic soap by a double decomposition process, comprising the steps of:

feeding an aqueous solution of an alkali soap and an inorganic metal salt directly onto the surface of a rotating impeller blade of a turbine pump to instantaneously mix said alkali soap and inorganic metal salt together and form a metallic soap aqueous slurry; and discharging the metallic soap aqueous slurry from the turbine pump without delay by means of a scraper blade attached to the rotor of the turbine pump.

2. A process as claimed in claim 1, wherein the inorganic metal salt/alkali soap equivalent ratio ranges from 0.95 to 1.05.

3. A process as claimed in claim 1, wherein the metallic soap aqueous slurry discharged from the pump is further mixed under heating to increase the particle size of the metallic soap particles.

4. A process as claimed in claim 3, wherein said mixing under heating is at a temperature of from 50° to 100° C.

5. A process as claimed in claim 1, wherein said rotating impeller blade and said scraper blade are the same element.

* * * * *